(12) United States Patent
Swager

(10) Patent No.: US 7,291,503 B2
(45) Date of Patent: Nov. 6, 2007

(54) REVERSIBLE RESISTIVITY-BASED SENSORS

(75) Inventor: Timothy M. Swager, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 603 days.

(21) Appl. No.: 10/442,678

(22) Filed: May 21, 2003

(65) Prior Publication Data
US 2004/0235184 A1    Nov. 25, 2004

(51) Int. Cl.
G01N 27/00    (2006.01)

(52) U.S. Cl. ............ 436/149; 436/150; 436/151; 422/82.02; 422/68.1; 422/82.01; 422/98; 204/400

(58) Field of Classification Search ........ 436/149–151; 422/82.02, 68.1, 82.01, 98; 204/400
See application file for complete search history.

(56) References Cited

U.S. PATENT DOCUMENTS

| | | | |
|---|---|---|---|
| 4,957,615 A * | 9/1990 | Ushizawa et al. ......... 204/415 |
| 5,026,783 A | 6/1991 | Grubbs et al. ........... 525/326.1 |
| 5,186,808 A * | 2/1993 | Yamaguchi et al. ..... 204/403.1 |
| 5,250,439 A * | 10/1993 | Musho et al. .............. 205/778 |
| 5,318,912 A * | 6/1994 | Silver et al. ............... 436/151 |
| 5,409,591 A | 4/1995 | Baker et al. ............... 204/425 |
| 5,418,366 A | 5/1995 | Rubin et al. ............... 250/338.5 |
| 5,453,220 A | 9/1995 | Swager et al. ............. 252/582 |
| 5,466,350 A | 11/1995 | Baker et al. ........... 204/153.14 |
| 5,491,097 A * | 2/1996 | Ribi et al. .................. 436/518 |
| 5,519,147 A | 5/1996 | Swager et al. ................ 549/59 |
| 5,565,075 A | 10/1996 | Davis et al. ................ 204/412 |
| 5,571,568 A * | 11/1996 | Ribi et al. .................. 427/487 |
| 5,580,433 A | 12/1996 | Baker et al. ................ 204/425 |
| 5,582,170 A | 12/1996 | Soller .......................... 128/634 |
| 5,603,820 A * | 2/1997 | Malinski et al. ............ 205/781 |
| 6,002,817 A | 12/1999 | Kopelman et al. ............ 385/12 |
| 6,100,096 A | 8/2000 | Bollinger et al. ........... 436/116 |
| 6,160,255 A | 12/2000 | Sausa .................... 250/227.24 |
| 6,175,752 B1 * | 1/2001 | Say et al. .................... 600/345 |
| 6,323,309 B1 | 11/2001 | Swager et al. .............. 528/380 |
| 6,623,870 B1 | 9/2003 | Epstein et al. .............. 428/690 |
| 6,635,415 B1 | 10/2003 | Bollinger et al. ............... 435/4 |
| 6,636,652 B1 | 10/2003 | Kopelman et al. ............ 385/12 |
| 6,759,010 B2 * | 7/2004 | Lewis et al. ............. 422/82.02 |
| 2002/0040805 A1 | 4/2002 | Swager et al. .............. 174/110 |
| 2002/0150697 A1 | 10/2002 | Swager et al. ............... 428/1.1 |
| 2002/0182740 A1 | 12/2002 | Noire et al. ................. 436/106 |
| 2003/0178607 A1 | 9/2003 | Swager et al. .............. 252/582 |

* cited by examiner

Primary Examiner—Monique T. Cole
(74) Attorney, Agent, or Firm—Dana M. Gordon; Foley Hoag LLP

(57) ABSTRACT

One aspect of the present invention relates to a method for detecting the presence of an analyte by comparing the conductivity of a mixture containing an analyte and a sensor to the conductivity of the sensor in the absence of analyte. In certain embodiments, the sensor of the present invention consists of a complexing domain comprising a metal ion and a complexing agent and a conducting polymer, wherein the redox potential of the metal ion is similar to the redox potential of the conducting polymer. In one preferred embodiment, the presence of nitric oxide is detected by measuring the conducting change of a sensor comprising poly N,N'-ethylenebis(salicylidenimine) and cobalt. The poly N,N'-ethylenebis(salicylidenimine) cobalt sensors of the present invention are not adversely effected by the presence of water or oxygen.

58 Claims, 7 Drawing Sheets (i) 2-tributylstannylthiophene, cat. $Cl_2Pd(PPh_3)_2$, DMF, 80°C, 12 h, Ar, 55-60%;
(ii) 0.52 equiv ethylenediamine, benzene, RT, 12 h, 94%;
(iii) $Co(OAc)_2\cdot(H_2O)_4$, DMF, Ar, RT, 83%.

(i) 2-tributylstannylthiophene, cat. $Cl_2Pd(PPh_3)_2$, DMF, 80°C, 12 h, Ar, 55-60%;
(ii) 0.52 equiv ethylenediamine, benzene, RT, 12 h, 94%;
(iii) $Co(OAc)_2$-$(H_2O)_4$, DMF, Ar, RT, 83%.

(i) 2-tributylstannyl-3,4-ethylenedioxythiophene,
cat. $Cl_2Pd(PPh_3)_2$, DMF, 80°C, 12 h, Ar, 27%;
(ii) 0.52 equiv ethylenediamine, benzene, RT, 12 h, 94%; and
(iii) $Co(OAc)_2\text{-}(H_2O)_4$, DMF, Ar, RT, 83%.

REVERSIBLE RESISTIVITY-BASED SENSORS

GOVERNMENT SUPPORT

This invention was made with government support under Grant Number N00014-97-1-0174 awarded by the Navy. The government has certain rights to this invention.

BACKGROUND OF THE INVENTION

Nitric oxide (NO), a free radical gas that is short-lived in biological materials, has recently been identified as a molecule that plays a fundamental role in biological processes. As a result, research into the physiology and pathology of nitric oxide has grown. This research activity has created a demand for accurate and precise techniques for the detection and quantification of nitric oxide.

The use of spectrophotometry, chemilluminescence, and paramagnetic resonance methods for detecting nitric oxide in biology and medicine are well established. However, these techniques require that a sample of biological fluid, for example, the extracellular fluid in a tissue or the support buffer in a suspension of cells, must be analyzed removed from its biological context. Measurements made on such samples reflect nitric oxide concentration at a single time, and when assembled in a series make a discontinuous record. Therefore, these methods are not ideal for following rapid processes because changes in nitric oxide concentration are not observed if they occur between sampling points. Moreover, the ability to follow rapid changes in NO concentration is important because nitric oxide is unstable in the presence of oxygen, persisting only a few minutes or seconds in biological systems.

Recently, electrodes for the direct electrochemical detection of nitric oxide have been developed. The earliest of these electrodes, known colloquially as the "Shibuki electrode", uses a Pt electrode to oxidize nitric oxide at 800 mV and to register the resulting oxidation current. See K. Shibuki *Neuroscience Research* 1990, 9, 69-76. This sensor is of limited utility because it is subject to the destructive buildup of oxidation products from nitric oxide within the enclosed electrolyte surrounding the Pt electrode. More recently, a method has become available that uses a metalloporphyrin membrane. See T. Malinski et al. *Nature*, 1992, 358, 676-677; T. Malinski et al, "Nitric Oxide Measurement by Electrochemical Methods", Methods in Nitric Oxide Research, chapter 22 (1996); and Published International Patent Application No. WO 93/21518. This sensor is constructed by electrochemically depositing a metalloporphyrin, for example nickel-tetrakis (3-methoxy-4-hydroxyphenyl) porphyrin, on a carbon electrode, followed by coating the porphyrin surface with a layer of Nafion™ (Dupont). Direct measurements of nitric oxide with good sensitivity and selectivity have been reported using this porphyrinized electrode. Its disadvantages include the difficulty in handling the fragile micron-diameter carbon fibers, which require manipulation under a microscope with cold illumination (or under water) to eliminate thermal convection currents that disturb the fibers. In another instance, a biochemically-modified electrode has also been proposed that employs Cytochrome C as a nitric oxide sensor. See K. Miki et al. *J. Electroanal. Chem.*, 1993, 6, 703-705. Other methods for nitric oxide detection include using electrodes constructed of gold or platinum (See F. Pariente et al. *J. Electroanal. Chem*, 1994, 379, 191-197 and F. Bedioui et al. *J. Electroanal. Chem*, 1994, 377, 295-298) and a porphyrinic-based platinum-iridium electrode. See K. Ichimori et al, "Practical nitric oxide measurement employing a nitric oxide-selective electrode", Ref. Sci. Instrum., 65 (8) August 1994 and H. Miyoshi, *FEBS Letters*, 1994, 345, 47-49.

Recent developments in solid state materials technology indicates that these materials may serve a useful role as sensory devices for determining the presence of a variety of analytes. One class of potentially useful solid state materials is conducting polymers. These polymers typically include organic structures possessing a degree of unsaturation to allow electronic communication throughout a polymeric structure. Because polymers in general are synthesized from monomer components, the design of the conducting properties of a conducting polymer can be facilitated by engineering the monomer component to a desired specificity. Moreover, polymers containing both organic and metal ion components afford a larger number of variables over organic-based polymers through the incorporation of a diverse number of metal ions.

A variety of conducting polymers of different compositions and physical properties have been reported. Zotti et al. disclosed in situ conductivity of some polypyrroles and polythiophenes redox modified with pendant ferrocene groups. It was found that the electron hopping rate through the conductive polymer backbone is increased by a decrease of the ferrocene backbone distance and by conjugation of ferrocene with the backbone itself. Zotti et al. *Chem. Mater.* 1995, 7, 2309. Cameron et al. described a benzimidazole-based conjugated polymer with coordinated $[Ru(bpy)_2]^{2+}$ that provides direct electronic communication between the ruthenium complex and the polymer. Cameron et al. *Chem. Commun.* 1997, 303. Audebert et al. report a series of conducting polymers based on metal salen containing units comprising mononuclear copper$^{II}$, cobalt$^{II}$, nickel$^{II}$ and zinc$^{II}$ complexes. Under carefully chosen conditions, thick electroactive polymer deposits are formed upon electrochemical oxidation of the monomer in solution. Audebert et al. *New. J. Chem.* 1992, 16, 697. U.S. Pat. No. 5,549,851 discusses silicon containing polymers admixed with an amine compound. A highly conductive polymer composition is formed upon doping with an oxidizing dopant, typically iodine and ferric chloride. The composition has improved shapability and can form a highly conductive film or coating.

The integration of receptors into conducting polymer frameworks has been shown to produce materials which provide changes in physical characteristics upon binding of targeted analytes. Devynck et al. described a material containing Co(III) porphyrin sites. Variations in the Co(III)/Co (II) redox couple were observed upon exposure to pyridine and with changing pyridine concentrations. U.S. Pat. No. 4,992,244 discloses a chemical microsensor fabricated using Langmuir-Blodgett techniques. The chemical microsensor was a film based on dithiolene transition metal complexes that displayed differing degrees of current changes upon exposure to varying concentrations of a gas or vapor.

Despite numerous advances in polymeric materials as chemoresistive and sensory devices, there still remains a need to develop sensitive, selective sensors that measure analyte concentration in real time. One promising approach to developing such a sensor is through transition-metal containing conducting polymers. In certain instances, these materials are sensitive to small molecules, such as NO, and hence could be used in detection devices.

SUMMARY OF THE INVENTION

One aspect of the present invention relates to a method for detecting the presence of an analyte by comparing the conductivity of a mixture containing an analyte and a sensor to the conductivity of the sensor in the absence of analyte. The sensor of the present invention consists of a metal ion and a conducting polymer wherein the redox potential of the metal ion is similar to the redox potential of the conducting polymer. In one preferred embodiment, the presence of nitric oxide is detected by measuring the conducting change of a sensor comprising poly N,N'-ethylenebis(salicylidenimine) and cobalt. It is thought that binding of NO to the metal ion of the sensor causes the conductivity change. The poly N,N'-ethylenebis(salicylidenimine) cobalt sensor of the present invention is not adversely effected by the presence of water or oxygen. In addition, binding of NO to the sensor is reversible. As a result, this sensor or structurally similar sensors have excellent prospects as selective reversible NO detectors in aerobic aqueous environments.

BRIEF DESCRIPTION OF THE INVENTION

FIG. 3 depicts (A) Cyclic voltammogram of a thin film of polymer 1 in 0.1 M $Bu_4NPF_6$/MeCN on a platimun button electrode; and (B) Cyclic voltammogram of polymer 1 on a interdigitated microelectrode with 5 µm spacing.

Figure 4:
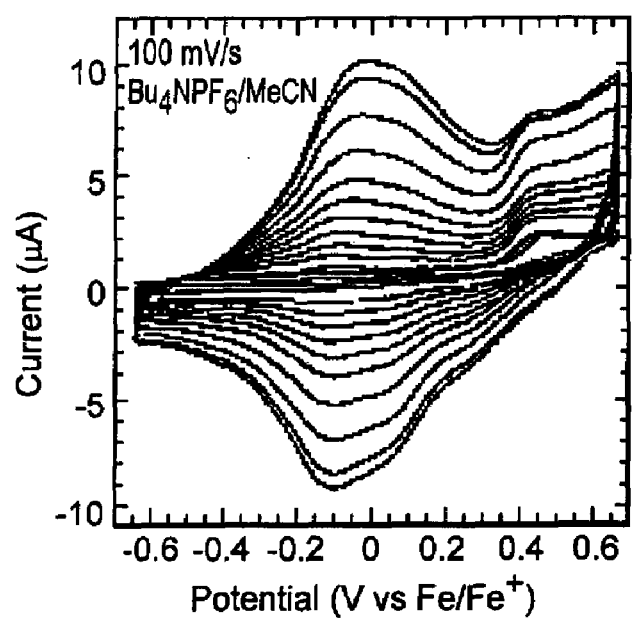

FIG. 4 depicts anodic polymerization of 7 on an interdigitated microelectrode with 5 mm spacing in 0.1 M $Bu_4NPF_6$/MeCN at a scan rate of 100 mV/s.

Figure 5A:
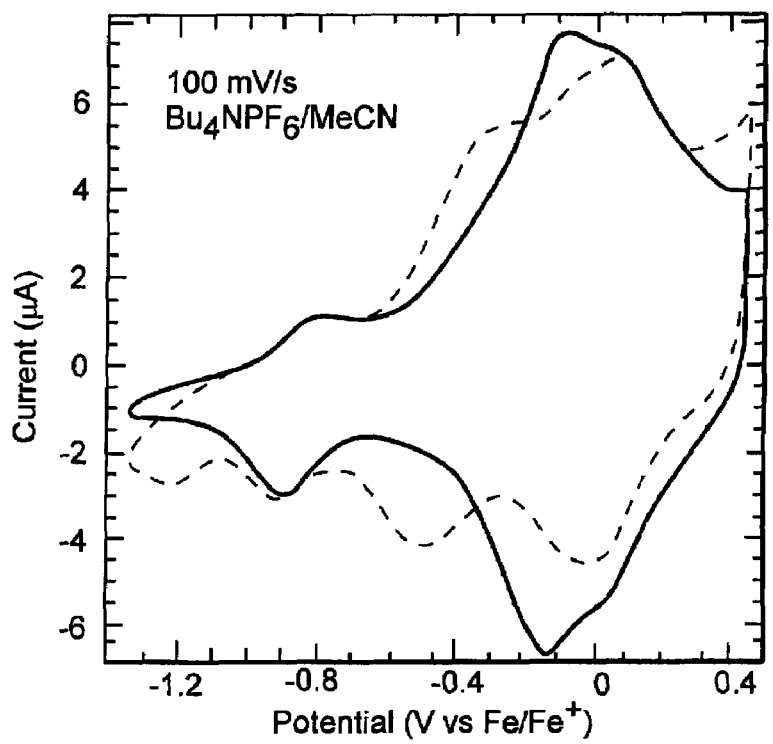

FIG. 5 depicts (A) cyclic voltammogram of polymer 8 on a platinum button electrode in 0.1 M $Bu_4NPF_6$/MeCN (solid line) and in the presence of 40 mM pyridine/Bu4NPF6/MeCN (dashed line), illustrating the presence of the cobalt-based redox wave; and (B) conductivity versus electrochemical potential of polymer 8 on an interdigitated microelectrode before (solid line) and after (dashed line) exposure to pyridine.

Figure 6:
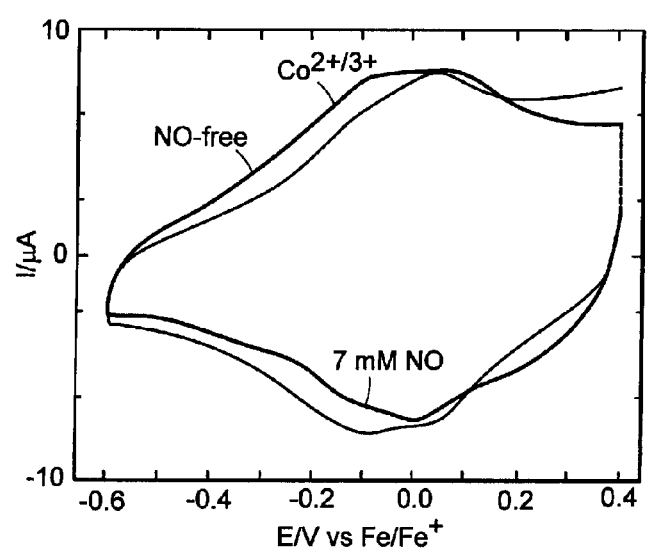

FIG. 6 depicts cyclic voltammetry of 8 in the absence and presence of NO. Note that $Co^{2+/3+}$ wave shifts from its initial position at about −0.1 V to being indistinguishable with the organic centered activity at 0.05 V in the presence of 7 mM NO.

Figure 7A:
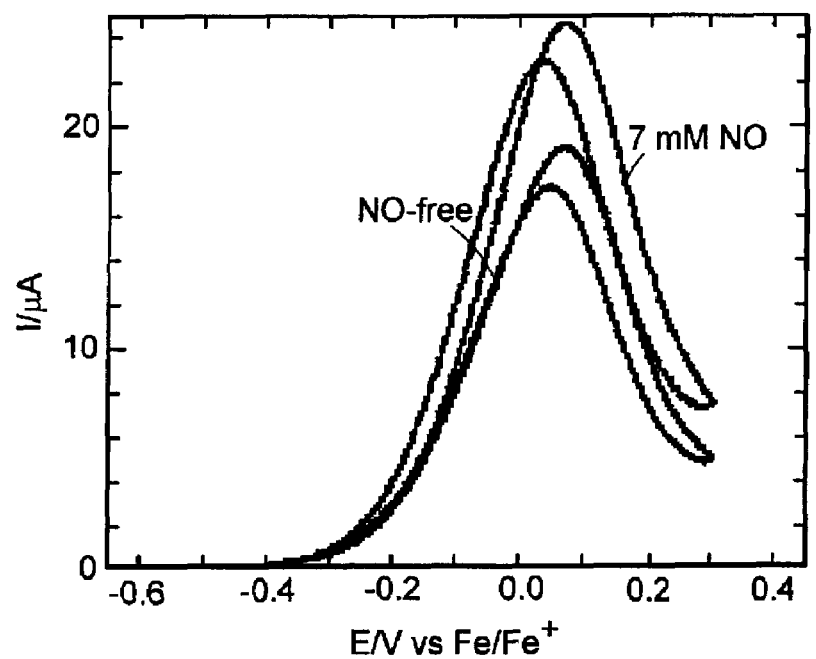
Figure 7B:
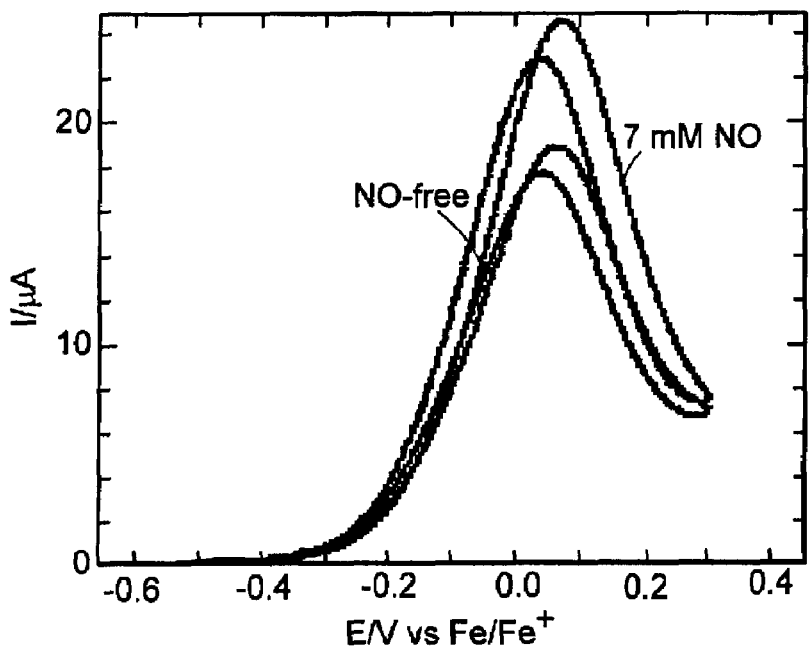

FIG. 7 depicts drain current profile (conductivity) of a microelectrochemical transistor base upon polymer 8 in the absence and presence of NO. The potential offset between microelectrodes was 40 mV and a sweep rate of 10 mV/s was used.

DETAILED DESCRIPTION OF THE INVENTION

The invention will now be described more fully with reference to the accompanying examples, in which certain preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Overview

The present invention relates generally to the detection of an analyte by measuring the resistance of a sensor compris-ing a metal ion and a conducting polymer. The analyte is detected when binding of the analyte to the sensor causes a change in the resistivity of the sensor. In the present invention, a sensor for nitric oxide has been developed in response to the interest in determining NO levels in biological systems. The NO sensor of the present invention is constructed of a cobalt-containing salen polymer film. This polymer has been shown to exhibit unique electrical properties because the redox potential of the chelating ligand is very similar to the $Co^{2+/3+}$ redox potential. Exposure of the sensor to NO in acetonitrile was shown to shift the $Co^{2+/3+}$ couple to more positive potentials in the cyclic voltammogram indicating that binding of NO to the sensor creates a better redox match with the organic centered electroactivity. In addition, the film rapidly returns to its original state when placed in a fresh NO-free electrolyte solution. Similar exposure of the sensor to a 7 mM solution of NO in acetonitrile produced an approximately 30% increase in conductivity and the response was reversible because the conductivity returned to normal after 5 electrochemical cycles (100 mV/sec) in a NO-free electrolyte. Additional studies have revealed that the sensor performs well in aqeous media and is not effected by oxygen concentration. As a result, this sensor or structually similar sensors have excellent prospects as selective reversible NO detectors in aerobic aqueous environments. A resistance-based method such as shown here could be used for monitoring of bulk NO concentrations, and should allow for microelectrode sensors to be produced that can be used to map out signals used in intercellular signaling.

Overview of a Preferred Embodiment

Nitric oxide (NO) serves as an intercellular signaling agent in a diverse array of living systems. M. Feelish, J. S. Stamler, Eds. *Methods in Nitric Oxide Research* John Wiley and Sons: Chichester, England, 1996; M. Lancaster, Ed. *Nitric Oxide: Principles and Actions* Academic Press, 1996. This recognition has stimulated considerable interest in the real-time detection of nitric oxide. Y. Katayama, S. Nobuaki, M. Maeda *Chem. Phys. Chem.* 2001, 2, 655-661. This mode of detection would find application in medical technology because increased levels of nitric oxide are known to be associated with up-regulation of the immune system. Thus, it is concievable that the early stages of a respiratory infection, e.g., SARS, may be detected by continously monitoring nitric oxide levels in the exhalate of an immune-compromised patient. C. Bogdan *Nature Immunoloogy* 2001, 2, 907-916.

A highly sensitive (ppm resolution), inexpensive NO sensor that conveys real-time measurements is ideal. In order to produce a real-time nitric oxide sensor, the sensor must exhibit specificity for NO and produce an easily detectable signal that responds to changes in the concentration of NO. Coordinatively unsaturated paramagnetic transition metal complexes are ideal candidates for recognizing (binding) nitric oxide, which has one unpaired electron in an antibonding orbital, because binding of NO to the transition metal complex influences the electrical properties (e.g., resistivity) of the complex.

In order to produce a resistance change in response to a metal-nitric oxide binding event, a system was designed, wherein the conductivity of the sensor intimately involves a transition metal ion. Pertinently, we have previously demonstrated that metal centers contribute to the electronic transport in conducting organic polymers when the redox activity of the metal center is coincident with that of an organic conducting polymer in its low resistance state. Kingsborough, K. P; Swager, T. M. *Adv. Mater.* 1998, 14, 1100-1104 and Zhu, S. S.; Swager, T. M. *J. Am. Chem. Soc.* 1997, 119, 12568-12577. When this redox-matching condition is met, the metal essentially provides additional electroactive pathways for transporting charge throughout the material. Hence, ligand binding events that produce changes in its redox potential can enhance or decrease the conductivity depending upon whether this process produces a better or worse match between the transition metal and the organic conducting polymer. Hence, this type of system appears to be ideally suited for nitric oxide detection.

A method for the detection of nitric oxide has been developed that involves measuring the conductivity of a solution containing NO and a sensor comprising a cobalt metal ion and a conducting polymer. Exposure of the sensor to a 7 mM solution of NO produced an approximately 30% increase in conductivity. The sensor displayed a reversible response to NO as the conductivity returns to normal after 5 electrochemical cycles (100 mV/sec) in NO-free electrolyte. This result has been interpreted to mean that NO binding to the cobalt center was reversible. In addition, the sensor of the present invention has been found to be very well behaved in aqueous systems. Interestingly, it has been found that the conductivity of the sensor is insensitive to oxygen concentration in both aqueous and organic media. As a result, this sensor or struturally similar sensors have excellent prospects to function as selective, reversible NO detectors in aerobic aqueous environments. A resistance-based method, such as dislcosed herein, will be useful for the monitoring of bulk NO concentrations. Further, this technology allows for microelectrode sensors to be produced that can be used to map out signals used in intercellular signaling.

Conducting Materials

One class of solid-state conducting materials is conducting polymers. These polymers typically include organic structures possessing a degree of unsaturation to allow electronic communication throughout a polymeric structure. Because polymers are synthesized from monomer components, the design of the conducting properties of a conducting polymer can be facilitated by engineering the monomer component to a desired specificity. Moreover, polymers containing both organic and metal ion components afford a larger number of variables over organic-based polymers through the incorporation of a diverse number of metal ions. The sensory polymer can be fabricated into an article containing another conducting element such as a carbon nanotube, carbon fibers, or gold particles. The system can be made to have a specific resistance due to the relative ratios of these different elements and exposure of the analyte to the polymer gives rise to a change in resistivity.

Polymers based on transition-metal-containing N,N'-ethylenebis(salicylidenimine) (salen) complexes have been previously prepared by the oxidative polymerization of monomeric M(salen) complexes. L. A. Hoferkamp, K. A. Goldsby *Chem. Mater.* 1989, 1, 348 and P. Audebert, P. Capdeville, M. Maumy *New J. Chem.* 1992, 16, 697. However, the majority of these polymers displayed ligand-based redox processes at high potentials that were considerably removed from the expected metal-based electroactivity. J. L. Reddinger, J. R. Reynolds *Chem. Mater.* 1998, 10, 3 and J. L. Reddinger, J. R. Reynolds *Chem. Mater.* 1998, 10. 1236. These films generally lacked metal-centered electroactivity. However, thin Co(salen) films did display redox processes attributed to the $Co^{2+/3+}$ couple that diminished as the films became progressively thicker. More recently, conducting polymers have been investigated that incorporate metal centers as part of the conduction pathway and tightly couple the conductivity to the redox characteristics of the metal center. Kingsborough, K. P.; Swager, T. M. *Adv. Mater.* 1998, 4, 10. It is believed that an organic polymer redox potential that is the same or below that of the metal center should create materials with enhanced electron mobilities, and thereby form optimized sensory and catalytic materials. Proof of this concept can be found in the above mentioned report by Swager wherein tuning the redox potential of the organic polymeric backbone to similar to that of the $Co^{2+/3+}$ redox potential resulted in enhanced electroactivity of cobalt centers. The intimate coupling of the metal and polymer in the conduction process can impart sensitivity to specific analytes, and it has been shown that Lewis bases, such as pyridine and substituted pyridines, affect the polymers' conductivity. Complexing agents such as optionally substituted phthalocyanines and porphyrins are logical alternatives to N,N'-ethylenebis(salicylidenimine).

Metal Ion

The metal ion could in principle be any transition metal, actinide, or lanthanide that can undergo oxidation/reduction. However, as noted above, it is important that the redox potential of the metal ion be similar to that of the conducting material. A list of suitable metals for use in the NO sensors of the present invnetion includes cobalt, iron, copper, nickel, ruthenium, iridium, manganese, chromium, molybdenum, vanadium, rhodium, and uranium. In certain preferred embodiments, the metal is cobalt.

Analyte

The analyte may be any molecule that binds to the sensor in such a way that the conductivity of the analyte-sensor complex is different than the conductivity of the sensor. The analyte could be in a solid, liquid, or gaseous physical state requiring only that the analyte be able to come into contact with the sensor for detection. The analyte could bind to the sensor through a vacant coordination site on the metal ion or to a portion of the conducting material. In the case of NO, it has been proposed that binding of NO to the cobalt metal ion influences the conductivity of the sensor by several different methods. In a first possibility, NO binding to the cobalt sensor creates a isoenergetic redox state that allows an additional mechanism for charge to transport through the system. A second possibility involves NO binding to the cobalt sensor resulting in a change in redox state from an isoenergetic one that is an integral part of the conduction pathway to one that is is not isoenergetic and hence is reduced (activated). Alternatively, NO binding to the cobalt sensor may liberate charge carriers in the sensor that are bound to a NO free cobalt sensor. However, NO binding to the cobalt sensor may result in the trapping of charge carriers with a NO bound cobalt sensor. In light of the many potential modes by which the analyte may influence the conductivity of the sensor, it is likely that the mode of action will be different for each analyte and involve a combination of factors. However, suitable analytes for detection include NO, CO, $CO_2$, $O_2$, $H_2O_2$, and $S(CH_3)_2$. In preferred embodiments, the analyte is NO.

Characterization of Metal-Containing Conducting Polymers by Cyclic Voltammetry

Figure 1:
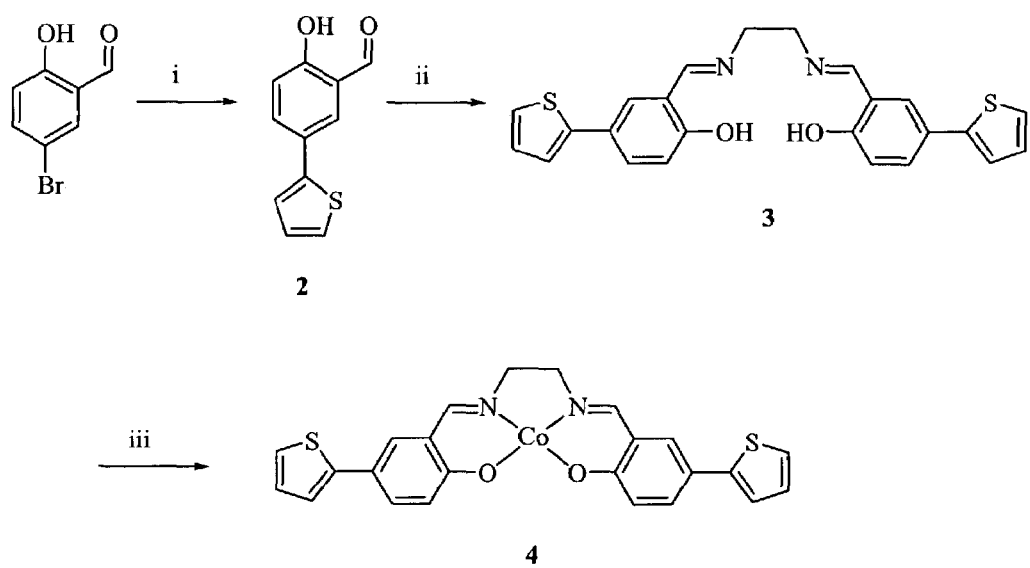
FIG. 1 depicts a synthesis of cobalt-salen complex 4.
Figure 2:
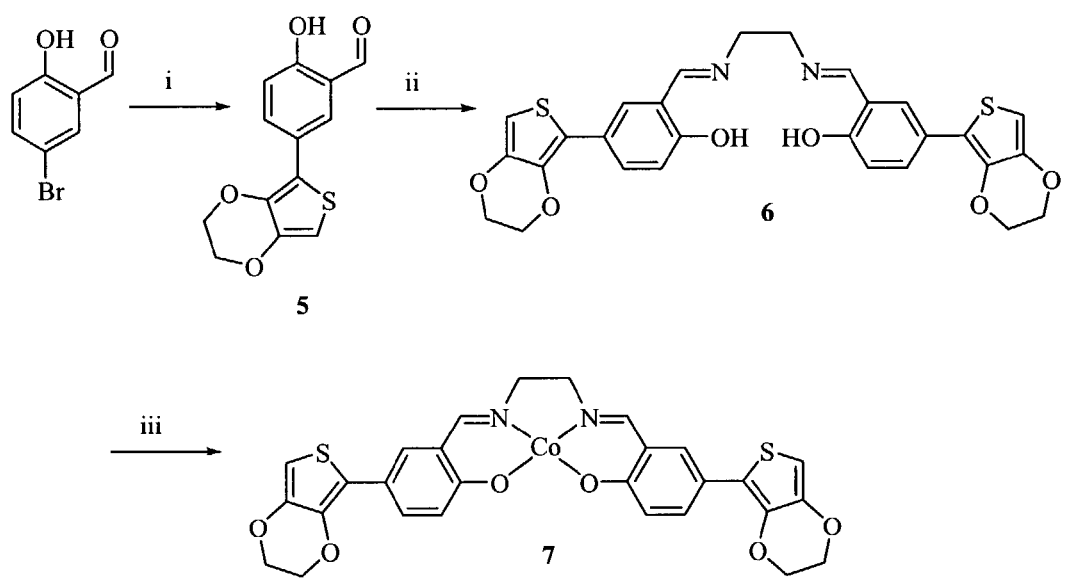
FIG. 2 depicts a synthesis of cobalt-salen complex 7.
Figure 3A:
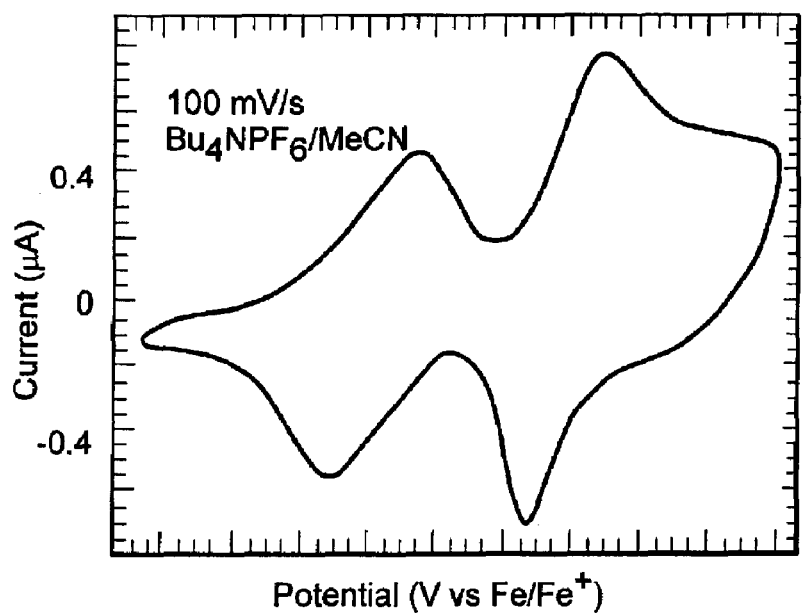
Figure 3B:
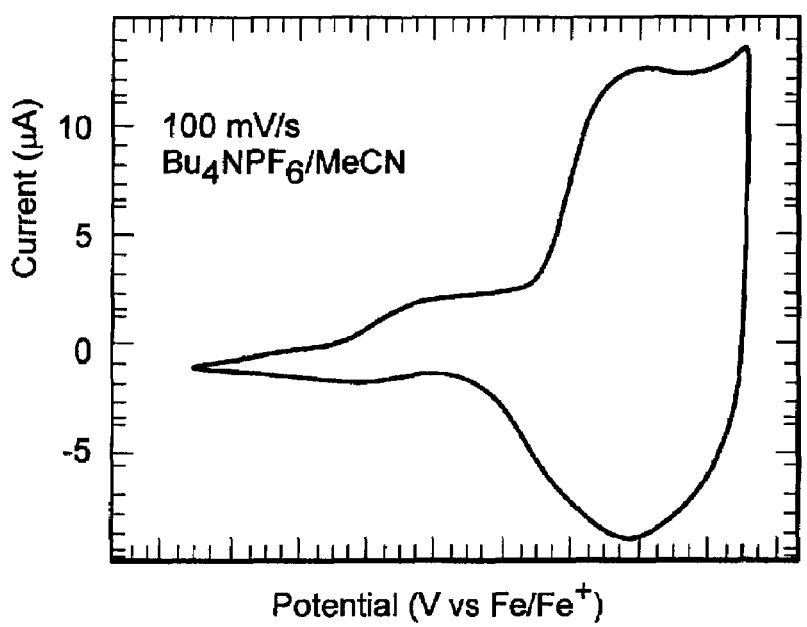

The cyclic voltammogram of a very thin film of sensory material 1 revealed that the ratio of metal to organic-centered redox waves to be approximately 1:2 (FIG. 3A). Upon growing a film sufficiently thick to connect two interdigitated electrodes, it was observed that the wave attributed to the $CO^{2+/3+}$ redox process was much smaller; also, a broad organic-based electrochemical process centered at 0.45 V was apparent. In addition, the ratio of metal to organic-centered redox waves was approximately 1:5 (FIG. 3B). The polymers displayed a broad, polythiophene-like CV trace, indicative of linear polymerization through the thiophene substituents. The polymer structure was indirectly confirmed by scanning a number of related transition metal complexes of the methyl-terminated salen ligand, N,N'-ethylenebis(5-(5-methylthienyl)salicylidenimine), to the same polymerization potentials. The absence of any polymer deposition supported the proposed structure and similar results have been reported in studies concerning the oxidative polymerization of M(salen) complexes.

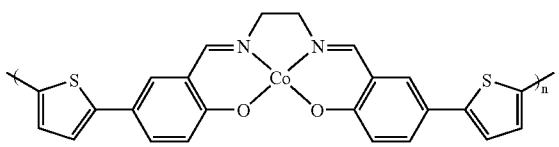

1

To account for the decreased electroactivity of the cobalt center in the thick films relative to the thin ones, it has been postulated that when the polymer is in the reduced state it effectively acts as an insulator, preventing the $Co^{2+/3+}$ redox process from occurring in a majority of the polymer structure. Those centers being oxidized or reduced are most likely very close to the electrode surface. It is believed that the remaining cobalt centers are irreversibly oxidized to $Co^{3+}$ during the polymerization process while the polymer is in its oxidized form, as it is more positive than the $Co^{2+/3+}$ redox couple. This phenomenon has also been observed by Horwitz and Murray. C. P. Horwitz, R. W. Murray, *Mol. Cryst. Liq. Cryst.* 1988, 160, 389.

Polymer 1 was prepared by polymerization of the corresponding monomer in 0.1 M $Et_4NPF_6$ electrolyte solutions in order to determine whether cation transport through the film was affecting the electroactivity of the $Co^{2+/3+}$ redox wave. Kingsborough, R. P.; Swager, T. M. *Adv. Mater.* 1998, 14, 10. In this case, there was a significant enhancement of the $Co^{2+/3+}$ wave relative to the polymer-based waves, even in films sufficiently thick to connect the microelectrodes. This enhancement was attributed to increased transport of the smaller cation or an overall morphological difference between the films grown in different electrolytes that allows all of the cobalt centers to undergo reversible redox processes while in the insulating regime of the polymer backbone. Although the exact nature of this enhancement was not specified, these results indicate that the films of 1 were sensitive to the electrolyte used in synthesis of the film.

Nitric Oxide Detectors as Medical Devices

Several medical devices are commercially available for the detection of nitric oxide. The ISO-NOPNM NanoSensor is a NO sensor that incorporates a composite graphite NO-sensing element, together with a built-in Ag/AgCl reference electrode. The surface of the sensing element is electrochemically 'activated' and then modified using a unique multi-layered NO-selective membrane. The response of the ISO-NOPNM following successive additions of nanomolar concentrations of NO. The response of the sensor was linear over the concentration range tested (0.5 nM to 1 μM) to successive additions of nanomolar concentrations of NO. One highly beneficial and intrinsic characteristic of the miniature size of the new NanoSensor, is that background noise of the sensor (which in most electrochemical sensors is proportional to their surface area) is greatly reduced to around just 0.5 pA. The ultra-low noise of the sensor enables an achievable lower detection limit of just 0.5 nM NO.

The ISO-NOPMC is a microchip-based NO electrode. It has a detection limit of less than 0.3 nM (300 pM) NO and is a very sensitive electrochemical NO sensor. The ISO-NOPMC is based on technology that utilizes a microelectrode wafer deposited on a single silicon chip. This new electrode exhibits good performance in the detection of NO. See Zhang, et al. (2000) "Integrated microchip NO sensor with enhanced sensitivity and selectivity." Nitric Oxide, 4:37, 278. The ISO-NOPMC's response (observed as peaks in the trace) following successive additions of 1.5 nM NO. ISO-NOPMC exhibits stable performance in sensitivity over the temperature ranges 20° C. to 40° C. and is particularly suited for real-time in situ monitoring of NO release in cell cultures and other similar applications where ultra-low detection of NO is required.

Definitions

For convenience, certain terms employed in the specification, examples, and appended claims are collected here.

The articles "a" and "an" are used herein to refer to one or to more than one (i.e. to at least one) of the grammatical object of the article. By way of example, "an element" means one element or more than one element.

The term "nanoparticle" refers to particles with physical size (e.g., diameter) of about 100 nanometers (nm) diameter or less.

The term "aerobic" refers to an atmosphere in which $O_2$ is present.

The term "anaerobic" refers to an atmosphere in which $O_2$ is not present.

The term "nanotube" refers to a particle with physical size (e.g., diameter) of about 100 nanometers (nm) diameter or less that has the shape of a tube.

The term "nanowire" refers to a particle with physical size (e.g., diameter) of about 100 nanometers (nm) diameter or less that has the shape of a wire.

The term "redox active" refers to a material that can undergo a change in oxidation state.

The term "semiconductor" refers to any class of solids whose electrical conductivity is between that of a conductor and that of an insulator in being nearly as great as that of a metal at high temperatures and nearly absent at low temperatures, as described by Marriam Webster's Collegiate Dictionary. $10^{th}$ Ed. Mish, F. C. 1993.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

The terms "aralkyl" and "arylalkyl", as used herein, refer to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that comprise a double or triple bond, respectively.

The term "aryl" as used herein includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles", "heteroaryl", or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, formyl, alkoxycarbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more rings in which two or more carbons are common to two adjoining rings (the rings are "fused") wherein at least one of the rings is aromatic, e.g., the other rings can be cycloalkyls, cycloalkenyls, cycloalkynyls, aryls and/or heterocyclyls.

For purposes of this invention, the chemical elements are identified in accordance with the Periodic Table of the Elements, CAS version, Handbook of Chemistry and Physics, 67th Ed., 1986-87, inside cover.

Methods of the Invention

One aspect of the present invention relates to a method for detecting the presence of an analyte in a mixture, comprising the steps of:

measuring the conductivity of a first mixture comprising a sensor; adding to said first mixture a sample optionally containing an analyte to generate a second mixture; measuring the conductivity of said second mixture; wherein said sensor comprises a plurality of alternating conducting domains and complexing domains; wherein each complexing domain independently consists of a metal ion and a complexing agent selected from the group consisting of N,N'-ethylenebis(salicylidenimine), phthalocyanine, and porphyrin; wherein each conducting domain is independently selected from the group consisting of a bond, carbon nanotube, carbon nanowire, carbon fiber, gold particle, poly N,N'-ethylenebis(salicylidenimine), polyphtbalocyanine, polyporphyrin, polyaniline, polythiophene, polypyrrole, polyphenylene, polyarylene, poly(bisthiophene phenylene), conjugated ladder polymer, polyiptycene, polytriphenylene, poly(arylene vinylene), and poly(arylene ethynylene).

In certain embodiments, said conducting domain is a block co-polymer.

In certain embodiments, said complexing agent is N,N'-ethylenebis(salicylidenimine).

In certain embodiments, said complexing agent is a bis-, tris-, tetra-, penta-, hexa-, hepta-, octa-, nona-, deca-, undeca-, or dodeca-(2-thiophen-5-yl)porphyrin.

In certain embodiments, said complexing agent is a bis-, tris-, tetra-, penta-, hexa-, hepta-, octa-, nona-, deca-, undeca-, or dodeca-(2-thiophen-5-yl)phthalocyanine.

In certain embodiments, said complexing agent is a bis-, tris-, tetra-, penta-, hexa-, hepta-, octa-, nona-, deca-, undeca-, or dodeca-(3-thiophen-5-yl)porphyrin.

In certain embodiments, said complexing agent is a bis-, tris-, tetra-, penta-, hexa-, hepta-, octa-, nona-, deca-, undeca-, or dodeca-(3-thiophen-5-yl)phthalocyanine.

In certain embodiments, said complexing agent is a bis (2-thiophen-5-yl)porphyrin.

In certain embodiments, said completing agent is a bis (2-thiophen-5-yl)phthalocyanine.

In certain embodiments, said complexing agent is a bis (3-thiophen-5-yl)porphyrin.

In certain embodiments, said complexing agent is a bis (3-thiophen-5-yl)phthalocyanine.

In certain embodiments, said metal ion is a transition metal, actinide, or lanthanide.

In certain embodiments, said metal ion is cobalt, iron, copper, nickel, ruthenium, iridium, manganese, chromium, molybdenum, vanadium, rhodium or uranium.

In certain embodiments, said metal ion is cobalt, rhodium, iron, copper, or nickel.

In certain embodiments, said metal ion is cobalt.

In certain embodiments, said complexing domain consists of said metal ion and said complexing agent is a N,N'-ethylenebis(salicylidenimine) represented by formula A:

wherein

M is a transition metal, actinide, or lanthanide;

R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —$COOR^1$, —$CO_2C(R^1)_3$, —$CONC(R^1)_2$, cyano, nitro, hydroxy, hydroxyalkyl, amino, alkylamino, dialkylamino, arylamino, diarylamino, —$NR^1COR^2$, thioalkyl, thioaryl, —$SO_2R^1$, —$SOR^1$, —$SO_2OR^1$, F, Cl, Br, or I; or two instances of R taken together form a ring structure;

$R^1$ and $R^2$ can be the same or different, and are each independently selected from the group consisting of hydrogen, $C_1$-$C_{10}$ alkyl, $C_1$-$C_{10}$ heteroalkyl, aryl, heteroaryl, hydroxy, F, Cl, Br, and I; and $R^3$ and $R^4$ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —$COOR^1$, —$CO_2C(R^1)_3$, —$CONC(R^1)_2$, cyano, nitro, hydroxy, hydroxyalkyl, amino, alkylamino, dialkylamino, arylamino, diarylamino, —$NR^1COR^2$, thioalkyl, thioaryl, —$SO_2R^1$, —$SOR^1$, —$SO_2OR^1$, F, Cl, Br, or I; or $R^3$ is connected to $R^4$ through a 1,2-dihydoxy ethylene bridge; or two instances of R taken together form a ring structure.

In certain embodiments, said complexing domain consists of said metal ion and said complexing agent is a N,N'-ethylenebis(salicylidenimine) represented by formula A, wherein R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, hydroxy, hydroxyalkyl, amino, alkylamino, dialkylamino, arylamino, diarylamino, —Oalkyl, —Oaryl, —Oheteroalkyl, —Oheteroaryl, —Oarylakyl, —$NR^1COR^2$, thioalkyl, or thioaryl; and $R^1$ and $R^2$ are independently selected from the group consisting of hydrogen, $C_1$-$C_{10}$ alkyl, $C_1$-$C_{10}$ heteroalkyl, aryl, and heteroaryl.

In certain embodiments, said complexing domain consists of said metal ion and said complexing agent is a N,N'-ethylenebis(salicylidenimine) represented by formula A, wherein M is cobalt, iron, copper, nickel, ruthenium, iridium, manganese, chromium, molybdenum, vanadium, rhodium, or uranium.

In certain embodiments, said complexing domain consists of said metal ion and said complexing agent is a N,N'-ethylenebis(salicylidenimine) represented by formula A, wherein M is cobalt, rhodium, iron, copper, or nickel.

In certain embodiments, said complexing domain consists of said metal ion and said complexing agent is a N,N'-ethylenebis(salicylidenimine) represented by formula A, wherein M is cobalt.

In certain embodiments, said complexing domain consists of said metal ion and said complexing agent is a N,N'-ethylenebis(salicylidenimine) represented by formula A, wherein R represents independently for each occurrence hydrogen;

$R^3$ is connected to $R^4$ through a —$OCH_2CH_2O$— bridge; and

M is cobalt.

In certain embodiments, said complexing domain consists of said metal ion and said complexing agent is a N,N'-ethylenebis(salicylidenimine) represented by formula A, wherein R represents independently for each occurrence hydrogen;

$R^3$ is connected to $R^4$ through a —$OCH_2CH_2O$— bridge;

M is cobalt; and said conducting domain is poly N,N'-ethylenebis(salicylidenimine).

In certain embodiments, said complexing domain consists of said metal ion and said complexing agent is a N,N'-ethylenebis(salicylidenimine) represented by formula A, wherein R represents independently for each occurrence hydrogen;

$R^3$ is connected to $R^4$ through a —$OCH_2CH_2O$— bridge;

M is cobalt; and said conducting domain is a bond.

In certain embodiments, said complexing domain consists of said metal ion and said complexing agent is a phthalocyanine represented by formula D:

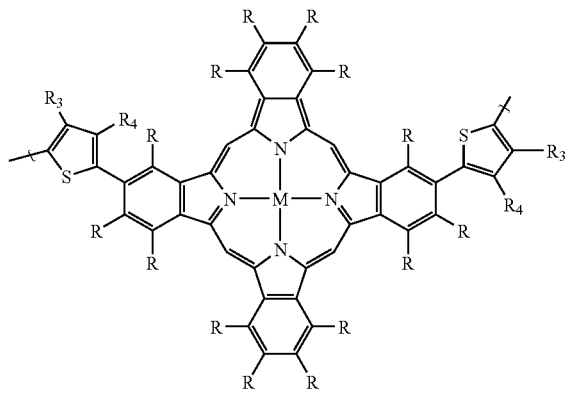

D wherein

M is a transition metal, actinide, or lanthanide;

R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —$COOR^1$, —$CO_2C(R^1)_3$, —$CONC(R^1)_2$, cyano, nitro, hydroxy, hydroxyalkyl, amino, alkylamino, dialkylamino, arylamino, diarylamino, —$NR^1COR^2$, thioalkyl, thioaryl, —$SO_2R^1$, —$SOR^1$, —$SO_2OR^1$, F, Cl, Br, or I; or two instances of R taken together form a ring structure;

$R^1$ and $R^2$ can be the same or different, and are each independently selected from the group consisting of hydrogen, $C_1$-$C_{10}$ alkyl, $C_1$-$C_{10}$ heteroalkyl, aryl, heteroaryl, hydroxy, F, Cl, Br, and I; and $R^3$ and $R^4$ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —$COOR^1$, —$CO_2C(R^1)_3$, —$CONC(R^1)_2$, cyano, nitro, hydroxy, hydroxyalkyl, amino, alkylamino, dialkylamino, arylamino, diarylamino, —$NR^1COR^2$, thioalkyl, thioaryl, —$SO_2R^1$, —$SOR^1$, —$SO_2OR^1$, F, Cl, Br, or I; or $R^3$ is connected to $R^4$ through a 1,2-dihydoxy ethylene bridge; or two instances of R taken together form a ring structure.

In certain embodiments, wherein said complexing domain consists of said metal ion and said complexing agent is a phthalocyanine represented by formula E:

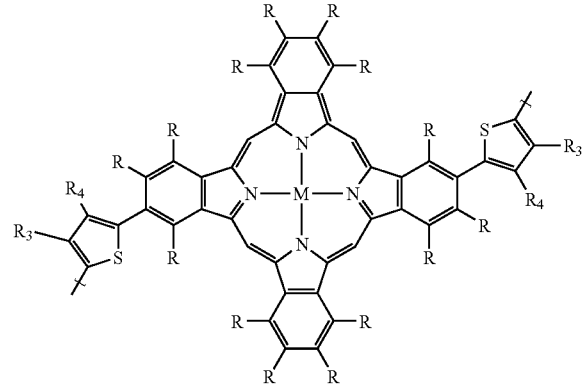

E wherein

M is a transition metal, actinide, or lanthanide;

R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —$COOR^1$, —$CO_2C(R^1)_3$, —$CONC(R^1)_2$, cyano, nitro, hydroxy, hydroxyalkyl, amino, alkylamino, dialkylamino, arylamino, diarylamino, —$NR^1COR^2$, thioalkyl, thioaryl, —$SO_2R^1$, —$SOR^1$, —$SO_2OR^1$, F, Cl, Br, or I; or two instances of R taken together form a ring structure;

$R^1$ and $R^2$ can be the same or different, and are each independently selected from the group consisting of hydrogen, $C_1$-$C_{10}$ alkyl, $C_1$-$C_{10}$ heteroalkyl, aryl, heteroaryl, hydroxy, F, Cl, Br, and I; and $R^3$ and $R^4$ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —$COOR^1$, —$CO_2C(R^1)_3$, —$CONC(R^1)_2$, cyano, nitro, hydroxy, hydroxyalkyl, amino, alkylamino, dialkylamino, arylamino, diarylamino, —$NR^1COR^2$, thioalkyl, thioaryl, —$SO_2R^1$, —$SOR^1$, —$SO_2OR^1$, F, Cl, Br, or I; or $R^3$ is connected to $R^4$ through a 1,2-dihydoxy ethylene bridge; or two instances of R taken together form a ring structure.

In certain embodiments, wherein said complexing domain consists of said metal ion and said complexing agent is a porphyrin is represented by formula F:

F

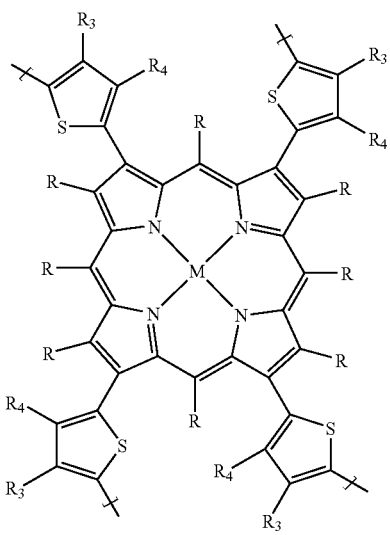

wherein

M is a transition metal, actinide, or lanthanide;

R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$^1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or two instances of R taken together form a ring structure;

R$^1$ and R$^2$ can be the same or different, and are each independently selected from the group consisting of hydrogen, $C_1$-$C_{10}$ alkyl, $C_1$-$C_{10}$ heteroalkyl, aryl, heteroaryl, hydroxy, F, Cl, Br, and I; and R$^3$ and R$^4$ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$^1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or R$^3$ is connected to R$^4$ through a 1,2-dihydoxy ethylene bridge; or two instances of R taken together form a ring structure.

In certain embodiments, said complexing domain consists of said metal ion and said complexing agent is a porphyrin is represented by formula H:

H

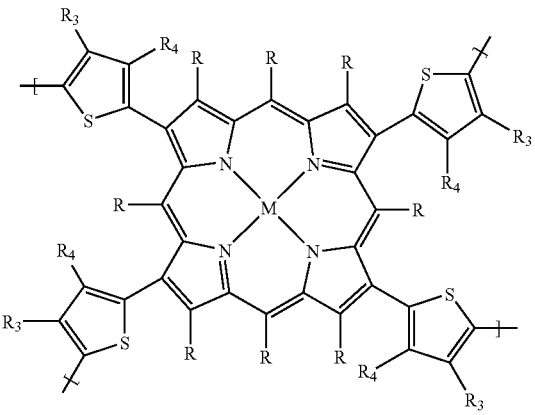

wherein

M is a transition metal, actinide, or lanthanide;

R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$^1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or two instances of R taken together form a ring structure;

R$^1$ and R$^2$ can be the same or different, and are each independently selected from the group consisting of hydrogen, $C_1$-$C_{10}$ alkyl, $C_1$-$C_{10}$ heteroalkyl, aryl, heteroaryl, hydroxy, F, Cl, Br, and I; and R$^3$ and R$^4$ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$^1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or R$^3$ is In certain embodiments, said complexing domain consists of said metal ion and said complexing agent is a porphyrin is represented by formula G:

G

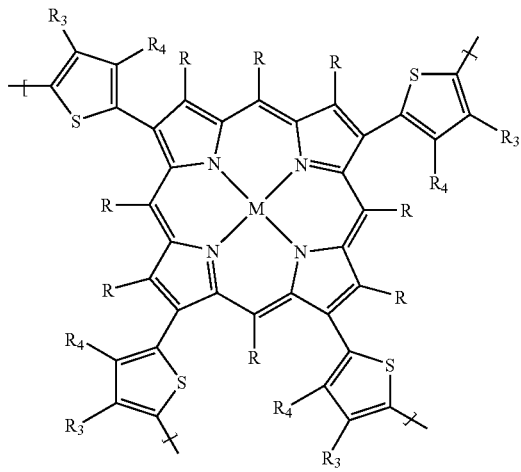

connected to R⁴ through a 1,2-dihydoxy ethylene bridge; or two instances of R taken together form a ring structure.

In certain embodiments, said complexing domain consists of said metal ion and said complexing agent is a porphyrin is represented by formula I:

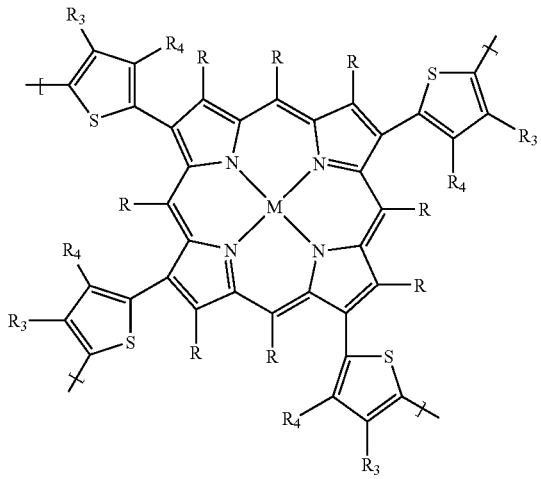

I wherein

M is a transition metal, actinide, or lanthanide;

R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR¹, —CO₂C(R¹)₃, —CONC(R¹)₂, cyano, nitro, hydroxy, hydroxyalkyl, amino, alkylamino, dialkylamino, arylamino, diarylamino, —NR¹COR², thioalkyl, thioaryl, —SO₂R¹, —SOR¹, —SO₂OR¹, F, Cl, Br, or I; or two instances of R taken together form a ring structure;

R¹ and R² can be the same or different, and are each independently selected from the group consisting of hydrogen, $C_1$-$C_{10}$ alkyl, $C_1$-$C_{10}$ heteroalkyl, aryl, heteroaryl, hydroxy, F, Cl, Br, and I; and R³ and R⁴ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR¹, —CO₂C(R¹)₃, —CONC(R¹)₂, cyano, nitro, hydroxy, hydroxyalkyl, amino, alkylamino, dialkylamino, arylamino, diarylamino, —NR¹COR², thioalkyl, thioaryl, —SO₂R¹, —SOR¹, —SO₂OR¹, F, Cl, Br, or I; or R₃ is connected to R₄ through a 1,2-dihydoxy ethylene bridge; or two instances of R taken together form a ring structure.

In certain embodiments, said complexing domain consists of said metal ion and said complexing agent is a porphyrin is represented by formula J:

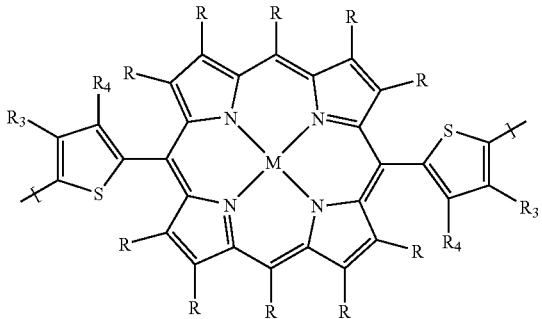

J wherein

M is a transition metal, actinide, or lanthanide;

R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR¹, —CO₂C(R¹)₃, —CONC(R¹)₂, cyano, nitro, hydroxy, hydroxyalkyl, amino, alkylamino, dialkylamino, arylamino, diarylamino, —NR¹COR², thioalkyl, thioaryl, —SO₂R¹, —SOR¹, —SO₂OR¹, F, Cl, Br, or I; or two instances of R taken together form a ring structure;

R¹ and R² can be the same or different, and are each independently selected from the group consisting of hydrogen, $C_1$-$C_{10}$ alkyl, $C_1$-$C_{10}$ heteroalkyl, aryl, heteroaryl, hydroxy, F, Cl, Br, and I; and R³ and R⁴ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR¹, —CO₂C(R¹)₃, —CONC(R¹)₂, cyano, nitro, hydroxy, hydroxyalkyl, amino, alkylamino, dialkylamino, arylamino, diarylamino, —NR¹COR², thioalkyl, thioaryl, —SO₂R¹, —SOR¹, —SO₂OR¹, F, Cl, Br, or I; or R³ is connected to R⁴ through a 1,2-dihydoxy ethylene bridge; or two instances of R taken together form a ring structure.

In certain embodiments, said analyte is NO, $CO_2$, CO, $O_2$, $H_2O_2$, or $S(CH_3)_2$.

In certain embodiments, said analyte is NO or CO.

In certain embodiments, said analyte is NO.

In certain embodiments, said first mixture comprises water or a polar aprotic solvent.

In certain embodiments, said first mixture comprises an aprotic solvent.

In certain embodiments, the redox potential of said metal ion differs from the redox potential of said complexing agent by less than about 250 mV.

In certain embodiments, the redox potential of said metal ion differs from the redox potential of said complexing agent by less than about 175 mV.

In certain embodiments, the redox potential of said metal ion differs from the redox potential of said complexing agent by less than about 100 mV.

In certain embodiments, the redox potential of said metal ion differs from the redox potential of said complexing agent by less than about 50 mV.

In certain embodiments, the redox potential of said metal ion differs from the redox potential of said complexing agent by less than about 15 mV.

In certain embodiments, said analyte is NO; and the concentration of said NO in said second mixture is less than about 500 μM.

In certain embodiments, said analyte is NO; and the concentration of said NO in said second mixture is less than about 200 μM.

In certain embodiments, said analyte is NO; and the concentration of said NO in said second mixture is less than about 75 μM.

In certain embodiments, said analyte is NO; and the concentration of said NO in said second mixture is less than about 30 μM.

In certain embodiments, said analyte is NO; and the concentration of said NO in said second mixture is less than about 15 μM.

In certain embodiments, said analyte is NO; and the concentration of said NO in said second mixture is less than about 7 μM.

In certain embodiments, said analyte is NO; and the concentration of said NO in said second mixture is less than about 3 μM.

In certain embodiments, said first mixture is aerobic; and said second mixture is aerobic.

In certain embodiments, said first mixture is anaerobic; and said second mixture is anaerobic.

In certain embodiments, at least 99% of said metal ions are redox active.

In certain embodiments, at least 75% of said metal ions are redox active.

In certain embodiments, at least 50% of said metal ions are redox active.

In certain embodiments, at least 25% of said metal ions are redox active.

In certain embodiments, at least 10% of said metal ions are redox active.

In certain embodiments, said analyte binds to said metal ion of said sensor.

In certain embodiments, said metal ion comprises a free coordination site.

In certain embodiments, binding of said analyte on at least 1% of the free coordination sites on said metal ion results in a conductivity change through the polymeric structure of at least 1%.

In certain embodiments, the conductivity of said sensor is at least $10^{-2}$ Scm$^{-1}$.

In certain embodiments, the conductivity of said sensor is at least $10^{-4}$ Scm$^{-1}$.

In certain embodiments, the conductivity of said sensor is at least $10^{-6}$ Scm$^{-1}$.

In certain embodiments, a first electrode is connected to a first portion of said sensor and a second electrode is connected to a second portion of said sensor; said first electrode is connected to said second electrode by an electrical circuit external of said sensor; and a source of electric potential in the electrical circuit and a two-point conductivity probe (or generic measuring device).

Exemplification

The invention now being generally described, it will be more readily understood by reference to the following examples, which are included merely for purposes of illustration of certain aspects and embodiments of the present invention, and are not intended to limit the invention.

Synthesis of Polymer 5-(2-Thienyl)salicylaldehyde (2): To a mixture of 5-bromosalicylaldehyde (2.847 g, 14.16 mmol) and Cl$_2$Pd(PPh$_3$)$_2$ (0.497 g, 0.708 mmol, 0.05 equiv) was added tributylstannyl thiophene (6.75 mL, 21.24 mmol, 1.5 equiv) in 25 mL of DMF. The reaction mixture was heated at 80° C. for 16 h, over which time the reaction color changed from light yellow to dark red. The reaction was cooled, diluted with Et$_2$O and washed with dilute NH$_4$Cl (4×150 mL). The organic layer was collected and filtered through a short silica pad to yield a yellow filtrate. The solvent was removed under reduced pressure to afford a gummy yellow solid, which was transferred to a frit and washed with hexanes. The yellow solid was dried in vacuo to afford 1.895 g (9.28 mmol, 66%) of a yellow powder (mp 102-103° C.). $^1$H NMR (250 MHz, CDCl$_3$) δ 11.01 (s, 1H), 9.96 (s, 1H), 7.80-7.76 (m, 2H), 7.29-7.24 (m, 2H), 7.09 (dd, 1H, J=3.8 and 5.1 Hz), 7.04 (dd, 1H, J=2.5 and 7.0 Hz). $^{13}$C NMR (62 MHz, CDCl$_3$) δ 196.5, 161.1, 142.7, 134.7, 130.8, 128.3, 127.1, 124.8, 123.0, 120.8, 118.4. UV-Vis (MeCN) $\lambda_{max}$ 210, 252, 289, 361 nm. MS m/z 204 (M$^+$). HRMS (FAB) found m/z 205.0324 (M+H$^+$); calcd for C$_{11}$H$_9$O$_2$S m/z 205.0323 ([M+H]$^+$). Elemental anal. calcd for C$_{11}$H$_9$O$_2$S: C, 64.69; H, 3.95. Found: C, 64.76; H, 3.78.

5-(2-(3,4-Ethylenedioxy)thienyl)salicylaldehyde (5): This compound was prepared in similar fashion to 2 except that 2-tributylstannyl-3,4-ethylenedioxythiophene was used in place of thiophene. (27%), mp 132° C., dec. $^1$H NMR (250 MHz, CDCl$_3$) δ 10.98 (s, 1H), 9.94 (s, 1H), 7.92 (d, 1H, J=2.3 Hz), 7.84 (dd, 1H, J=2.4 and 8.7 Hz), 7.00 (d, 1H, J=8.7 Hz), 6.29 (s, 1H), 4.34-4.25 (m, 4H). $^{13}$C NMR (125 MHz, CDCl$_3$) δ 197.1, 160.4, 142.6, 138.2, 134.9, 131.1, 125.9, 120.8, 118.2, 115.8, 97.5, 65.1, 64.7. UV-Vis (MeCN) $\lambda_{max}$ 214, 257, 295, 373 nm. MS m/z 262 (M$^+$). HRMS (FAB) found m/z 263.0378 (M+H$^+$); calcd for C$_{13}$H$_{11}$O$_4$S m/z 263.0378 ([M+H]$^+$). Elemental anal. calcd. for C$_{13}$H$_{11}$O$_4$S: C, 59.53; H, 3.84. Found: C, 59.35; H, 3.86.

The ligands and metal complexes were prepared by literature procedures from the appropriate salicylaldehyde. See D. J. Aymes, M. R. Paris, *J. Chem. Ed.* 1989, 66, 854. b) C. Floriani, F. Calderazzo, *J. Chem. Soc.* 1969, 946.

N,N'-Ethylenebis(5-(2-thienyl)salicylidenimine) (3): 94% yellow powder, mp 255° C., dec. $^1$H NMR (250 MHz, CDCl$_3$) δ 13.29 (s, 2H), 8.43 (s, 2H), 7.55 (dd, 2H, J=2.4 and 8.4 Hz), 7.46 (d, 2H, J=2.3 Hz), 7.22-7.16 (m, 4H), 7.05 (dd, 2H, J=3.6 and 5.0 Hz), 6.97 (d, 2H, J=8.7 Hz), 3.99 (s, 4H). The poor solubility of this compound prevented characterization by $^{13}$C NMR. UV-Vis (MeCN) $\lambda_{max}$ 252, 293 nm. MS m/z 432 (M$^+$). HRMS (EI) found m/z 432.0964 (M$^+$); calcd for C$_{24}$H$_{20}$N$_2$O$_2$S$_2$ (M$^+$) 432.0966. Elemental anal. calcd. for C$_{24}$H$_{20}$N$_2$O$_2$S$_2$: C, 66.64; H, 4.66; N, 6.48. Found: 66.43; H, 4.35; N, 6.34.

N,N'-Ethylenebis(5-(2-(3,4-ethylenedioxy)thienyl)salicylidenimine) (6): 94% yellow solid, mp 245° C., dec. $^1$H NMR (250 MHz, CDCl$_3$) δ 13.26 (s, 2H), 8.41 (s, 2H), 7.63-7.60 (m, 4H), 6.95 (d, 2H, J=8.3 Hz), 6.22 (s, 2H), 4.35-4.22 (m, 8H), 3.97 (s, 4H). The poor solubility of this compound prevented characterization by $^{13}$C NMR. MS m/z 549 ([M+H]$^+$). HRMS (FAB) found m/z 549.1157 ([M+H]$^+$); calcd for C$_{28}$H$_{25}$N$_2$O$_6$S$_2$ m/z 549.1154 ([M+H]$^+$).

N,N'-Ethylenebis(5-(2-thienyl)salicylideniminato)cobalt (II) (4): 83% black microcrystalline solid, mp>250° C. UV-Vis (MeCN) $\lambda_{max}$ 261, 315, 389, 415 nm. MS m/z 489 (M$^+$). HRMS (EI) found m/z 489.0144 (M$^+$); calcd for C$_{24}$H$_{18}$CoN$_2$O$_2$S$_2$ (M$^+$) 489.0142. Elemental anal. calcd for C$_{24}$H$_{18}$CoN$_2$O$_2$S$_2$: C, 58.89; H, 3.71; N, 5.72. Found: C, 58.76; H, 3.94; N, 6.11.

N,N'-Ethylenebis(5-(2-(3,4-ethylenedioxy)thienyl)salicylideniminato)cobalt(II) (7): 83% green-black microcrystalline solid, mp>250° C. UV-Vis (MeCN) $\lambda_{max}$ 267, 317, 398 nm. HRMS (LDMS) found m/z 605.02 (M$^+$); calcd for C$_{24}$H$_{18}$CoN$_2$O$_2$S$_2$ (M$^+$) 605.54. Elemental anal. calcd for C$_{28}$H$_{22}$CoN$_2$O$_6$S$_2$: C, 55.54; H, 3.66; N, 4.63. Found: C, 54.73; H, 3.67; N, 4.56.

Cobalt salen polymer 1: Thin films of polymer 1 were obtained by oxidative deposition on platinum electrodes from a saturated monomer solution (4 ca. 0.1 mM) in 0.1 M Bu$_4$NPF$_6$/MeCN by scanning between −0.75 V and 0.85 V under a nitrogen atmosphere and all electrochemical data is referred to ferrocene/ferrocenium (Fc/Fc$^+$). The cyclic voltammogram of a very thin film of polymer 1 reveals that the ratio of metal to organic-centered redox waves to be approximately 1:2 (FIG. 3A). The polymer structure was indirectly confirmed by scanning a number of related transition metal complexes of the methyl-terminated salen ligand, N,N'-ethylenebis(5-(5-methylthienyl)salicylidenimine), to the same polymerization potentials. The absence of any polymer deposition supports the proposed structure and similar results have been reported in studies concerning the oxidative polymerization of M(salen) complexes. See L. A. Hoferkamp, K. A. Goldsby, *Chem. Mater.* 1989, 1, 348; K. A. Goldsby, J. K. Blaho, J. K. Hoferkamp, *Polyhedron* 1989, 8, 113; P. Audebert, P. Capdeville, M. Maumy, *New J. Chem.* 1991, 15, 235; C. E. Dahm, D. G. Peters, *Anal. Chem.* 1994, 66, 3117; J. L. Reddinger, J. R. Reynolds, *Chem. Mater.* 1998, 10, 3; and J. L. Reddinger, J. R. Reynolds, *Chem. Mater.* 1998, 10. 1236

Figure 5B:
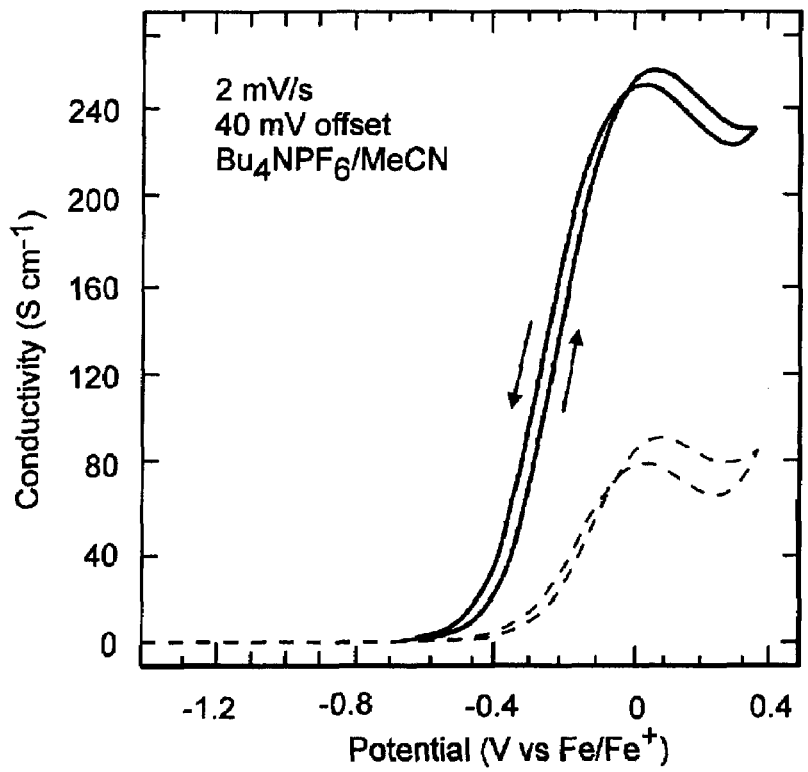

Cobalt salen polymer 8: Cobalt salen polymer 8 was prepared by electrochemical polymerization (FIG. 4) of saturated solutions of 7 ([7] ca. 0.1 mM). As can be seen in Scheme 4a, the redox potential of the polymer 8 backbone has been significantly lowered to almost perfectly coincide with the $Co^{2+/3+}$ redox wave. Close inspection of the CV trace reveals that there are two redox waves seen at −0.11 V and 0.07 V, due to the $Co^{2+/3+}$ and polymer redox processes, respectively. The identity of the $Co^{2+/3+}$ wave was revealed by the addition of pyridine (FIG. 5A), resulting in a shift of the wave at −0.11 V to lower potential (−0.38 V), consistent with shifts observed in monomeric systems. See E. Eichhorn, A. Rieker, B. Speiser, H. Stahl, *Inorg. Chem.* 1997, 36, 3307. Also observed in the cyclic voltammogram at lower potentials (−0.84 V) is a wave that has been assigned to the $Co^{+/2+}$ redox transition. In similar fashion to polymer 1 films, it appears that only a small fraction of the cobalt centers can undergo this additional redox process in the thicker films. The conductivity of the polymer 8 film on interdigitated microelectrodes shows a broad trace increasing from ca. −0.4 V through a maximum at 0.05 V and a subsequent decrease to a high plateau at higher potentials (FIG. 5B).

Electrochemical Characterization of Polymer Solution

All of the electrochemical experiments were performed in acetonitrile with 0.1 M $TBAPF_6$ electrolyte. The procedure of Ford and coworkers was used to purify nitric oxide from a cylinder. Lorkovic, I. M.; Ford, P. C. *Inorg. Chem.* 2000, 39, 632. Infrared spectroscopy (1 atm NO in a 10 cm pathlength gas cell) was used to determine that the other nitrogen oxides had been completely removed. The purified NO was collected in a acetonitrile solution ([NO]≈7 mM) and its relative concentration was determined using cyclic voltammetry ($E°=0.867$ V vs. $Fc/Fc^+$, 0.1 M $TBAPF_6$).

As shown in FIG. 6, polymer 8 displays two closely spaced peaks in its cyclic voltammogram. The peak centered at approximately −0.1 V corresponds to the $Co^{2+/3+}$ couple and the peak at 0.05 V is assigned to the organic portion of the polymer. This assignment was previously confirmed by the fact that exposure to pyridine shifts the cobalt centered waves to less positive potentials while leaving the organic centered redox processes untouched. As shown in FIG. 6, exposure to NO shifts the $Co^{2+/3+}$ couple to more positive potentials and effectively creates a better redox match with the organic centered electroactivity. The film rapidly returns to its original state upon placing it in fresh NO-free electrolyte. The observed shift of the $Co^{2+/3+}$ wave to positive potential is consistent with the NO binding to the cobalt center. The highest energy electron of this nominally square planar species is in the $dz^2$ orbital and bonding of this unpaired electron with the NO radical thereby gives a complex with an overall higher oxidation potential. It appears that upon oxidation the complex remains intact as the reduction wave assigned to NO-free cobalt center is not observed in the presence of NO. This indicates that both the $Co^{2+}$ and the oxidized $Co^{3+}$ centers have strong binding affinities to NO.

8

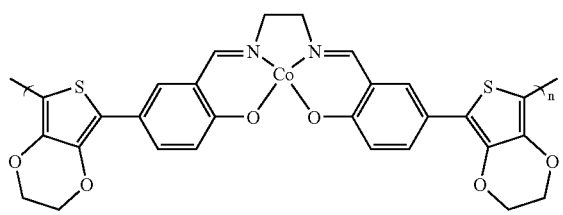

Consistent with our redox matching model the improved overlap between the cobalt and the organic ligand's electroactivity enhances the materials conductivity. FIG. 7 shows measurements of the relative conductivity of thin films deposited on an array of interdigitated microelectrodes. These devices are effectively electrochemical transistors with the applied electrochemical potential functioning as the gate voltage and the current flowing between the source and drain electrodes is directly proportional to the conductivity. G. P. Kittlesen, H. S. White, M. S. Wrighton, *J. Am. Chem. Soc.* 1984, 106, 7389. We have previously found Polymer 8 to display a peak conductivity of 40 S/cm. As can be seen in FIG. 7, exposure of a microelectrochemical transistor to a 7 mM NO solution produces approximately 30% increase in conductivity. The sensor displays a highly reversible response and as shown in FIG. 7 the conductivity returns to normal after 5 electrochemical cycles (100 mV/sec) in NO-free electrolyte. As a result, the NO binding to the cobalt center is highly reversible.

Polymer 8 has been found to be very well behaved in aqueous systems and we previously have shown that it also functions as a highly effect catalyst for oxygen reduction at more negative potentials. Kingsborough, R. P.; Swager, T. M. *Chem. Mater.* 2000, 12, 872-874. Interesting in both aqueous and organic media we have found that the conductivity of polymer 8 is insensitive to oxygen concentration.

Additional Patents and Publications Cited

1. *Handbook of Conducting Polymers*, 2nd ed. (Eds: T. A. Skotheim, R. L. Elsenbaumer, J. R. Reynolds), Marcel Dekker, New York 1998.
2. P. Audebert *Curr. Top. Electrochem.* 1994, 3, 459.
3. D. M. Kelley, J. G. Vos, in *Electroactive Polymer Electrochemistry*, (Ed: M. E. Lyons), Plenum, New York 1994, Vol. 2.
4. M. Lyons, in *Electroactive Polymer Electrochemistry*, (Ed: M. E. Lyons), Plenum, New York 1994, Vol. 1.

Incorporation by Reference

All of the patents and publications cited herein are hereby incorporated by reference.

Equivalents

Those skilled in the art will recognize, or be able to ascertain using less than routine experimentation, many equivalents to the specific embodiments of the invention described herein. Such equivalents are intended to be encompassed by the following claims.

I claim:

1. A method for detecting the presence of an analyte in a sample, comprising the steps of:
   measuring the conductivity of a first mixture comprising aqueous or organic media and a sensor;
      wherein said sensor comprises a plurality of alternating conducting domains and complexing domains; wherein each complexing domain independently consists of a metal ion and a complexing agent selected from the group consisting of N,N'-ethylenebis(salicylidenimine), phthalocyanine, (2-thiophen-5-yl)porphyrin and (3-thiophen-5-yl) porphyrin; wherein each conducting domain is independently selected from the group consisting of a bond, carbon nanotube, carbon nanowire, carbon fiber, gold particle, poly N,N'-ethylenebis(salicylidenimine), polyphthalocyanine, poly(2-thiophen-5-yl)porphyrin, poly(3-thiophen-5-yl)porohyrin, polyaniline, polythiophene, polypyrrole, polyphenylene, polyarylene, poly(bisthiophene phenylene), conjugated ladder polymer, polyiptycene, polytriphenylene, poly(arylene vinylene), and poly (arylene ethynylene);

adding to said first mixture said sample optionally containing an analyte to generate a second mixture;
measuring the conductivity of said second mixture;
determining whether an analyte is present in said sample by comparing the conductivity of said first mixture to the conductivity of said second mixture.

2. The method of claim 1, wherein said conducting domain is a block co-polymer.

3. The method of claim 1, wherein said complexing agent is a N,N'-ethylenebis(salicylidenimine).

4. The method of claim 1, wherein said complexing agent is a bis-, tris-, tetra-, penta-, hexa-, hepta-, octa-, nona-, deca-, undeca-, or dodeca-(2-thiophen-5-yl)porphyrin.

5. The method of claim 1, wherein said complexing agent is a bis-, tris-, tetra-, penta-, hexa-, hepta-, octa-, nona-, deca-, undeca-, or dodeca-(2-thiophen-5-yl)phthalocyanine.

6. The method of claim 1, wherein said complexing agent is a bis-, tris-, tetra-, penta-, hexa-, hepta-, octa-, nona-, deca-, undeca-, or dodeca-(3-thiophen-5-yl)porphyrin.

7. The method of claim 1, wherein said complexing agent is a bis-, tris-, tetra-, penta-, hexa-, hepta-, octa-, nona-, deca-, undeca-, or dodeca-(3-thiophen-5-yl)phthalocyanine.

8. The method of claim 1, wherein said complexing agent is a bis(2-thiophen-5-yl)porphyrin.

9. The method of claim 1, wherein said complexing agent is a bis(2-thiophen-5-yl)phthalocyanine.

10. The method of claim 1, wherein said complexing agent is a bis(3-thiophen-5-yl)porphyrin.

11. The method of claim 1, wherein said complexing agent is a bis(3-thiophen-5-yl)phthalocyanine.

12. The method of claim 1, wherein said metal ion is a transition metal, actinide, or lanthanide.

13. The method of claim 1, wherein said metal ion is cobalt, iron, copper, nickel, ruthenium, iridium, manganese, chromium, molybdenum, vanadium, rhodium or uranium.

14. The method of claim 1, wherein said metal ion is cobalt, rhodium, iron, copper, or nickel.

15. The method of claim 1, wherein said complexing domain consists of said metal ion and said complexing agent is a N,N'-ethylenebis(salicylidenimine) represented by formula A:

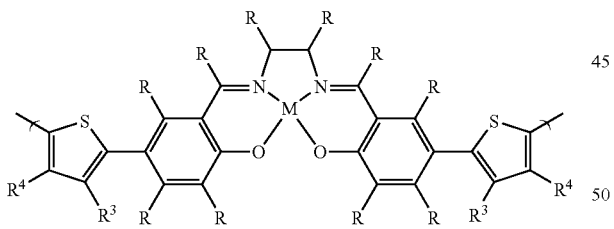

wherein
M is a transition metal, actinide, or lanthanide;
R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$^1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or two instances of R taken together form a ring structure;
R$^1$ and R$^2$ can be the same or different, and are each independently selected from the group consisting of hydrogen, $C_1$-$C_{10}$ alkyl, $C_1$-$C_{10}$ heteroalkyl, aryl, heteroaryl, hydroxy, F, Cl, Br, and I; and
R$^3$ and R$^4$ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$^1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or R$_3$ is connected to R$_4$ through a 1,2-dihydoxy ethylene bridge; or two instances of R taken together form a ring structure.

16. The method of claim 15, wherein
R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, hydroxy, hydroxyalkyl, amino, alkylamino, dialkylamino, arylamino, diarylamino, —Oalkyl, —Oaryl, —Oheteroalkyl, —Oheteroaryl, —Oarylakyl, —NR$^1$COR$^2$, thioalkyl, or thioaryl; and
R$^1$ and R$^2$ are independently selected from the group consisting of hydrogen, $C_1$-$C_{10}$ alkyl, $C_1$-$C_{10}$ heteroalkyl, aryl, and heteroaryl.

17. The method of claim 15, wherein M is cobalt, iron, copper, nickel, ruthenium, iridium, manganese, chromium, molybdenum, vanadium, rhodium, or uranium.

18. The method of claim 15, wherein M is cobalt, rhodium, iron, copper, or nickel.

19. The method of claim 15, wherein M is cobalt.

20. The method of claim 15, wherein
R represents independently for each occurrence hydrogen;
R$^3$ is connected to R$^4$ through a —OCH$_2$CH$_2$O— bridge; and
M is cobalt.

21. The method of claim 15, wherein
R represents independently for each occurrence hydrogen;
R$^3$ is connected to R$^4$ through a —OCH$_2$CH$_2$O— bridge;
M is cobalt; and
said conducting domain is poly N,N'-ethylenebis(salicylidenimine).

22. The method of claim 15, wherein
R represents independently for each occurrence hydrogen;
R$^3$ connected to R$^4$ through a —OCH$_2$CH$_2$O— bridge;
M is cobalt; and
said conducting domain is a bond.

23. The method of claim 1, wherein said complexing domain consists of said metal ion and said complexing agent is a phthalocyanine represented by formula D:

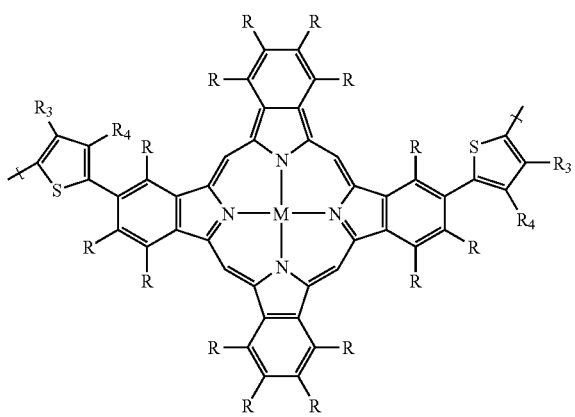

wherein
M is a transition metal, actinide, or lanthanide;

R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$^1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or two instances of R taken together form a ring structure;

R$^1$ and R$^2$ can be the same or different, and are each independently selected from the group consisting of hydrogen, $C_1$-$C_{10}$ alkyl, $C_1$-$C_{10}$ heteroalkyl, aryl, heteroaryl, hydroxy, F, Cl, Br, and I; and R$^3$ and R$^4$ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$^1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or R$_3$ is connected to R$_4$ through a 1,2-dihydoxy ethylene bridge; or two instances of R taken together form a ring structure.

24. The method of claim 1, wherein said complexing domain consists of said metal ion and said complexing agent is a phthalocyanine represented by formula E:

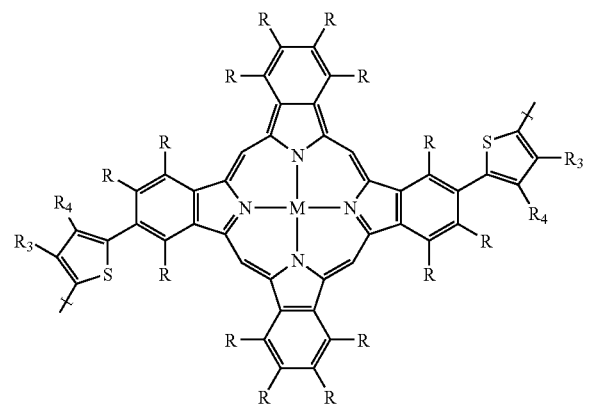

wherein

M is a transition metal, actinide, or lanthanide;

R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$^1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or two instances of R taken together form a ring structure;

R$^1$ and R$^2$ can be the same or different, and are each independently selected from the group consisting of hydrogen, $C_1$-$C_{10}$ alkyl, $C_1$-$C_{10}$ heteroalkyl, aryl, heteroaryl, hydroxy, F, Cl, Br, and I; and R$^3$ and R$^4$ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$_1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or R$_3$ is connected to R$_4$ through a 1,2-dihydoxy ethylene bridge; or two instances of R taken together form a ring structure.

25. The method of claim 1, wherein said complexing domain consists of said metal ion and said complexing agent is a (2-thiophen-5-yl)porphyrin represented by formula F:

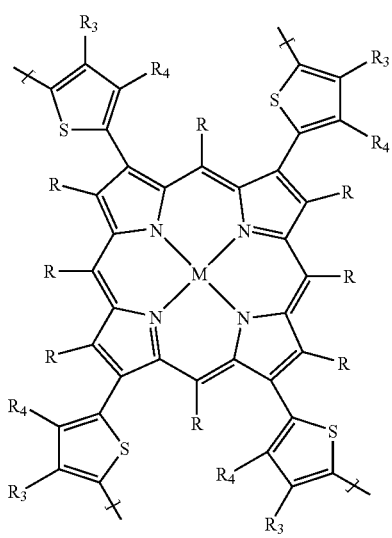

wherein

M is a transition metal, actinide, or lanthanide;

R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$_1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or two instances of R taken together form a ring structure;

R$^1$ and R$^2$ can be the same or different, and are each independently selected from the group consisting of hydrogen, $C_1$-$C_{10}$ alkyl, $C_1$-$C_{10}$ heteroalkyl, aryl, heteroaryl, hydroxy, F, Cl, Br, and I; and R$^3$ and R$^4$ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$^1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or R$^3$ is connected to R$^4$ through a 1,2-dihydoxy ethylene bridge; or two instances of R taken together form a ring structure.

26. The method of claim 1, wherein said complexing domain consists of said metal ion and said complexing agent is a (2-thiophen-5-yl)porphyrin represented by formula G:

G

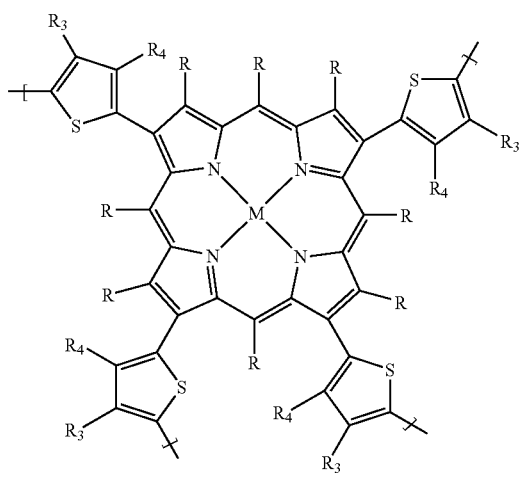

wherein
M is a transition metal, actinide, or lanthanide;
R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$^1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or two instances of R taken together form a ring structure;
R$^1$ and R$^2$ can be the same or different, and are each independently selected from the group consisting of hydrogen, $C_1$-$C_{10}$ alkyl, $C_1$-$C_{10}$ heteroalkyl, aryl, heteroaryl, hydroxy, F, Cl, Br, and I; and
R$^3$ and R$^4$ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$_1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or R$_3$ is connected to R$_4$ through a 1,2-dihydoxy ethylene bridge; or two instances of R taken together form a ring structure.

27. The method of claim 1, wherein said complexing domain consists of said metal ion and said complexing agent is a (2-thiophen-5-yl)porphyrin represented by formula H:

H

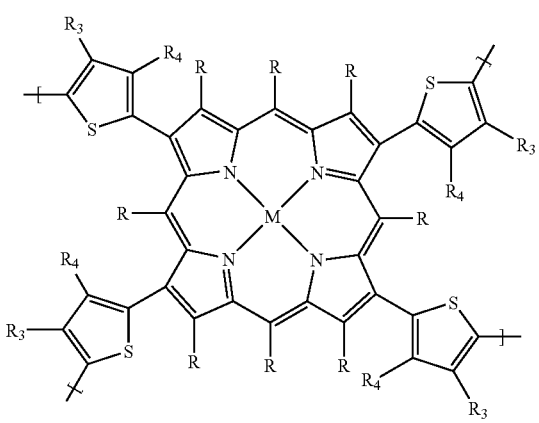

wherein
M is a transition metal, actinide, or lanthanide;
R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$^1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or two instances of R taken together form a ring structure;
R$^1$ and R$^2$ can be the same or different, and are each independently selected from the group consisting of hydrogen, $C_1$-C,o alkyl, $C_1$-$C_{10}$ heteroalkyl, aryl, heteroaryl, hydroxy, F, Cl, Br, and I; and
R$^3$ and R$^4$ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$^1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or R$_3$ is connected to R$_4$ through a 1,2-dihydoxy ethylene bridge; or two instances of R taken together form a ring structure.

28. The method of claim 1, wherein said complexing domain consists of said metal ion and said complexing agent is a (2-thiophen-5-yl)porphyrin represented by formula I:

I

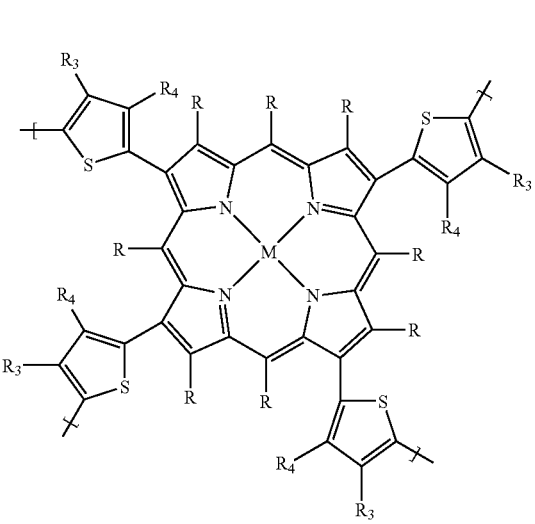

wherein
M is a transition metal, actinide, or lanthanide;
R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR$^1$, —CO$_2$C(R$^1$)$_3$, —CONC(R$^1$)$_2$, cyano, nitro, hydroxy, hydroxyalkyl, amino, alkylamino, dialkylamino, arylamino, diarylamino, —NR$^1$COR$^2$, thioalkyl, thioaryl, —SO$_2$R$^1$, —SOR$^1$, —SO$_2$OR$^1$, F, Cl, Br, or I; or two instances of R taken together form a ring structure;
R$^1$ and R$^2$ can be the same or different, and are each independently selected from the group consisting of hydrogen, $C_1$-$C_{10}$ alkyl, $C_1$-$C_{10}$ heteroalkyl, aryl, heteroaryl, hydroxy, F, Cl, Br, and I; and R³ and R⁴ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR¹, —CO$_2$C(R¹)$_3$, —CONC(R¹)$_2$, cyano, nitro, hydroxy, hydroxyalkyl, amino, alkylamino, dialkylamino, arylamino, diarylamino, —NR¹COR², thioalkyl, thioaryl, —SO$_2$R¹, —SOR¹, —SO$_2$OR¹, F, Cl, Br, or I; or R$_3$ is connected to R$_4$ through a 1,2-dihydoxy ethylene bridge; or two instances of R taken together form a ring structure.

29. The method of claim 1, wherein said complexing domain consists of said metal ion and said complexing agent is a (2-thiophen-5-yl)porphyrin represented by formula J:

J

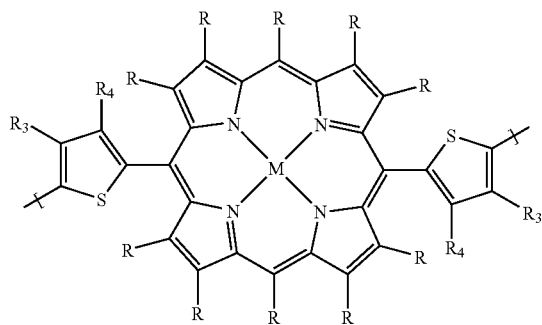

wherein

M is a transition metal, actinide, or lanthanide;

R represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR¹, —CO$_2$C(R¹)$_3$, —CONC(R¹)$_2$, cyano, nitro, hydroxy, hydroxyalkyl, amino, alkylamino, dialkylamino, arylamino, diarylamino, —NR¹COR², thioalkyl, thioaryl, —SO$_2$R¹, —SOR¹, —SO$_2$OR¹, F, Cl, Br, or I; or two instances of R taken together form a ring structure;

R¹ and R² can be the same or different, and are each independently selected from the group consisting of hydrogen, $C_1$-$C_{10}$ alkyl, $C_1$-$C_{10}$ heteroalkyl, aryl, heteroaryl, hydroxy, F, Cl, Br, and I; and R³ and R⁴ represents independently for each occurrence hydrogen, $C_1$-$C_{10}$ alkyl, $C_1$-$C_{10}$ heteroalkyl, aryl, heteroaryl, formyl, alkoxycarbonyl, acyl, acyloxy, —Oalkyl, —Oaryl, —Oheteroalkyl, —Oheteroaryl, —Oarylakyl, —CHO, —COOR¹, —CO$_2$C(R¹)$_3$, —CONC(R¹)$_2$, cyano, nitro, hydroxy, hydroxyalkyl, amino, alkylamino, dialkylamino, arylamino, diarylamino, —NR¹COR², thioalkyl, thioaryl, —SO$_2$R¹, —SOR¹, —SO$_2$OR¹, F, Cl, Br, or I; or R$_3$ is connected to R$_4$ through a 1,2-dihydoxy ethylene bridge; or two instances of R taken together form a ring structure.

30. The method of claim 1, wherein said analyte is NO, $CO_2$, CO, $O_2$, $H_2O_2$, or $S(CH_3)_2$.

31. The method of claim 1, wherein said analyte is NO or CO.

32. The method of claim 1, wherein said analyte is NO.

33. The method of claim 1, wherein said first mixture comprises water or a polar aprotic solvent.

34. The method of claim 1, wherein said first mixture comprises a polar aprotic solvent.

35. The method of claim 1, wherein the redox potential of said metal ion differs from the redox potential of said complexing agent by less than about 250 mV.

36. The method of claim 1, wherein the redox potential of said metal ion differs from the redox potential of said complexing agent by less than about 175 mV.

37. The method of claim 1, wherein the redox potential of said metal ion differs from the redox potential of said complexing agent by less than about 100 mV.

38. The method of claim 1, wherein the redox potential of said metal ion differs from the redox potential of said complexing agent by less than about 50 mV.

39. The method of claim 1, wherein the redox potential of said metal ion differs from the redox potential of said complexing agent by less than about 15 mV.

40. The method of claim 1, wherein said analyte is NO; and the concentration of said NO in said second mixture is less than about 500 μM.

41. The method of claim 1, wherein said analyte is NO; and the concentration of said NO in said second mixture is less than about 200 μM.

42. The method of claim 1, wherein said analyte is NO; and the concentration of said NO in said second mixture is less than about 75 μM.

43. The method of claim 1, wherein said analyte is NO; and the concentration of said NO in said second mixture is less than about 30 μM.

44. The method of claim 1, wherein said analyte is NO; and the concentration of said NO in said second mixture is less than about 15 μM.

45. The method of claim 1, wherein said analyte is NO; and the concentration of said NO in said second mixture is less than about 7 μM.

46. The method of claim 1, wherein said analyte is NO; and the concentration of said NO in said second mixture is less than about 3 μM.

47. The method of claim 1, wherein said first mixture is aerobic; and said second mixture is aerobic.

48. The method of claim 1, wherein said first mixture is anaerobic; and said second mixture is anaerobic.

49. The method of claim 1, wherein at least 99% of said metal ions are redox active.

50. The method of claim 1, wherein at least 75% of said metal ions are redox active.

51. The method of claim 1, wherein at least 50% of said metal ions are redox active.

52. The method of claim 1, wherein at least 25% of said metal ions are redox active.

53. The method of claim 1, wherein at least 10% of said metal ions are redox active.

54. The method of claim 1, wherein said analyte binds to said metal ion of said sensor.

55. The method of claim 1, wherein the conductivity of said sensor is at least $10^{-2}$ S·cm$^{-1}$.

56. The method of claim 1, wherein the conductivity of said sensor is at least $10^{-4}$ S·cm$^{-1}$.

57. The method of claim 1, wherein the conductivity of said sensor is at least $10^{-6}$ S·cm$^{-1}$.

58. The method of claim 1, wherein a first electrode is connected to a first portion of said sensor and a second electrode is connected to a second portion of said sensor; said first electrode is connected to said second electrode by an electrical circuit external of said sensor; and a source of electric potential in the electrical circuit and a two-point conductivity probe or generic measuring device.

* * * * *